United States Patent
Ikeda

(10) Patent No.: US 7,359,481 B2
(45) Date of Patent: Apr. 15, 2008

(54) X-RAY IMAGE DIAGNOSTIC DEVICE

(75) Inventor: Shigeyuki Ikeda, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 6 days.

(21) Appl. No.: 10/558,361

(22) PCT Filed: May 25, 2004

(86) PCT No.: PCT/JP2004/007086

§ 371 (c)(1),
(2), (4) Date: Nov. 25, 2005

(87) PCT Pub. No.: WO2004/105609

PCT Pub. Date: Dec. 9, 2004

(65) Prior Publication Data

US 2007/0009092 A1    Jan. 11, 2007

(30) Foreign Application Priority Data

May 27, 2003    (JP)    ............................ 2003-148579

(51) Int. Cl.
*G01N 23/04* (2006.01)
(52) U.S. Cl. ...................... 378/62; 378/98.8
(58) Field of Classification Search ............... 378/98.7, 378/98.11, 98.12, 116, 62, 146, 98.8, 98
See application file for complete search history.

(56) References Cited

U.S. PATENT DOCUMENTS

| | | | | |
|---|---|---|---|---|
| 5,412,704 A | * | 5/1995 | Horbaschek | 378/98.2 |
| 5,602,895 A | * | 2/1997 | Fivez et al. | 378/98.4 |
| 6,031,891 A | * | 2/2000 | Roos et al. | 378/98.2 |
| 6,418,241 B1 | * | 7/2002 | Schreiner | 382/263 |
| 2002/0057761 A1 | * | 5/2002 | Danielsson | 378/146 |
| 2004/0008817 A1 | * | 1/2004 | Nagai | 378/98.5 |
| 2004/0174953 A1 | * | 9/2004 | Ikeda et al. | 378/98.8 |

FOREIGN PATENT DOCUMENTS

| | | |
|---|---|---|
| JP | 7-72562 | 3/1995 |
| JP | 2000-33083 | 2/2000 |
| JP | 2001-61823 | 3/2001 |

* cited by examiner

*Primary Examiner*—Hoon Song
(74) *Attorney, Agent, or Firm*—Antonelli, Terry, Stout & Kraus, LLP.

(57) ABSTRACT

An x-ray diagnostic imaging system with an x-ray irradiation unit for irradiating an object; an x-ray diaphragm unit for shielding the irradiated x-rays except for the x-rays irradiated on a portion used for obtaining an x-ray image of the object; an x-ray diaphragm setting unit for variably setting the portion to be shielded; an x-ray flat panel detector opposed to the x-ray irradiation unit via the object to be examined; an image processing unit for subjecting the x-ray image to an image processing; and a display unit displaying the x-ray image. The image processing unit includes a calculation unit reading out data of an x-ray detection element and calculating a line noise component from the read out data; and a line noise correction unit correcting a line noise of the x-ray image based on the line noise component calculated by the calculation unit.

17 Claims, 8 Drawing Sheets

X-RAY IMAGE DIAGNOSTIC DEVICE

TECHNICAL FIELD

The present invention relates to an x-ray diagnostic imaging system provided with an x-ray flat panel detector detecting x-rays passed through an object to be examined.

BACKGROUND ART

An x-ray flat panel detector which is an x-ray detector having a plurality of x-ray detection elements 2-dimensionally arrayed thereon is used in x-ray diagnostic imaging systems. In the x-ray flat panel detector, a line noise in column direction or in row direction of the arrayed x-ray detection elements is sometimes observed when displaying an x-ray image. Therefore, it is necessary to correct the line noise in the x-ray diagnostic imaging systems having the x-ray flat panel detector.

One example of the line noise correction is disclosed in Patent Literature 1. In Patent Literature 1, an x-ray imaging device having a structure that line noise correction is performed by shielding an x-ray detection element positioned in a certain portion of an x-ray flat panel detector with lead or the like and by using output data of the x-ray detection element in the shielded portion. Therefore, the portion of the data used in the line noise correction are read out is always fixed.

However, since the shielded portion is always fixed in Patent Literature 1, the output data of the x-ray detection element in the shielded portion is fixed. Thus, a change in portion (effective visual field) for obtaining an x-ray image of an object to be examined in the x-ray flat panel detector is not considered in Patent Literature 1.

Patent Literature 1: JP-A-2000-33083

DISCLOSURE OF THE INVENTION

An x-ray diagnostic imaging system of this invention comprises an x-ray irradiation unit for irradiating an object to be examined with x-rays; an x-ray diaphragm unit disposed in a direction of x-ray irradiation of the x-ray irradiation unit and shielding the irradiated x-rays except for the x-rays irradiated on a portion used for obtaining an x-ray image of the object to be examined; an x-ray diaphragm setting unit for variably setting the x-ray shielded portion to be shielded by the x-ray diaphragm unit; an x-ray flat panel detector opposed to the x-ray irradiation unit via the object to be examined and imaging x-rays passed through the object to be examined as an x-ray image; an image processing unit for subjecting the x-ray image obtained by the x-ray flat panel detector to an image processing; and a display unit displaying the x-ray image subjected to the image processing by the image processing unit, wherein the image processing unit comprises a calculation unit reading out data of an x-ray detection element of the x-ray flat panel detector corresponding to the x-ray shielded portion shielded by the x-ray diaphragm unit which is variably set by the x-ray diaphragm setting unit and calculating a line noise component from the read out data of the x-ray detection element; and a line noise correction unit correcting a line noise of the x-ray image based on the line noise component calculated by the calculation unit.

Thus, it is possible to perform precisely the line noise correction of the x-ray image by the use of the data of the shielded portion of the x-ray flat panel detector, the shielded portion being shielded by the x-ray diaphragm which is variably set by the x-ray diaphragm setting unit.

According to one preferred embodiment of this invention, the calculation unit includes interaction of a data portion read out as the line noise component from the x-ray flat panel detector with the x-ray diaphragm unit variably set by the x-ray diaphragm setting unit.

Thus, it is possible to obtain the data for the line noise correction interacted with the shielded portion shielded by the thus-operated x-ray diaphragm unit.

According to another preferred embodiment of this invention, the image processing unit further comprises a correction execution switching unit switching to execution/non-execution of the line noise correction based on an x-ray condition set to the x-ray irradiation unit.

By prescribing a setting for executing the line noise correction in an x-ray condition, the correction is brought into an on-state only in the case of a fluoroscopic mode even when the fluoroscopic mode and a radiographic mode are performed successively. Therefore, operability is improved since it is unnecessary to set necessity/non necessity of the correction every time the mode is changed.

According to another preferred embodiment of this invention, the image processing unit further comprises a scattered x-ray elimination processing unit identifying an area in which x-rays scattered by the object to be examined are generated on the x-ray flat panel detector corresponding to the x-ray shielded portion variably set by the x-ray diaphragm setting unit and eliminating the identified scattered x-ray generation area from the line noise component calculation performed by the calculation unit.

Thus, it is possible to obtain a high quality x-ray image since the data used in the line noise correction are not influenced by the scattered x-rays.

According to another preferred embodiment of this invention, the x-ray diagnostic imaging system further comprises a second x-ray diaphragm unit disposed between the object to be examined and the x-ray flat panel detector in addition to the x-ray diaphragm unit and shielding the x-rays scattered by the object to be examined, wherein the x-ray diaphragm setting unit variably sets a size of an x-ray shielded portion shielded by the second x-ray diaphragm unit.

Thus, since the second x-ray diaphragm mechanically eliminates the x-rays scattered by the object to be examined, it is possible to improve the accuracy of the line noise correction by covering only the scattered x-ray generation portion with the second x-ray diaphragm as well as by increasing the correction data by the use of the data of the covered portion as the data to be used for the line noise correction.

According to another preferred embodiment of this invention, the x-ray diagnostic imaging system further comprises an operation unit to be used by an operator for setting an x-ray condition to the x-ray irradiation unit, an aperture condition of the x-ray diaphragm unit to the x-ray diaphragm setting unit, and an operation condition to the image processing unit; and a control unit driving the x-ray irradiation unit, the x-ray diaphragm setting unit, and the image processing unit based on the conditions set by the operation unit.

Thus, it is possible to perform precisely the line noise correction of the x-ray image in accordance with the conditions set by the operation unit.

According to another preferred embodiment of this invention, the control unit causes the x-ray irradiation unit to irradiate the object to be examined with x-rays corresponding to the x-ray condition set by the operation unit; the x-ray flat panel detector detects x-ray image data of x-rays projected by the x-ray irradiation unit and passed through the object to be examined and data of the shielded portion shielded by the x-ray diaphragm unit; and the calculation unit calculates a line noise component from the shielded portion data detected by the x-ray flat panel detector.

Thus, it is possible to perform the line noise correction of the x-ray image with the use of the data of the shielded portion shielded by the x-ray diaphragm which is variably set by the x-ray diaphragm setting unit.

According to another preferred embodiment of this invention, the control unit controls the correction execution switching unit switching to execution/non-execution of the line noise correction based on the x-ray condition set by the operation unit.

By prescribing a setting for executing the line noise correction in the x-ray condition, the correction is brought into an on-state only in the case of a fluoroscopic mode even when the fluoroscopic mode and a radiographic mode are performed successively. Therefore, operability is improved since it is unnecessary to set necessity/non necessity of the correction every time the modes are changed.

According to another preferred embodiment of this invention, the control unit controls the scattered x-ray elimination processing unit identifying an area in which x-rays scattered by the object to be examined are generated on the x-ray detection element of the x-ray flat panel detector corresponding to the x-ray shielded portion variably set by the x-ray diaphragm setting unit and eliminating the identified scattered x-ray generation area from the line noise component statistical value calculation performed by the calculation unit.

Thus, it is possible to obtain a high quality x-ray image since the data used in the line noise correction are not influenced by the scattered x-rays.

According to another preferred embodiment of this invention, the x-ray diagnostic imaging system further comprises a second x-ray diaphragm unit disposed between the object to be examined and the x-ray flat panel detector in addition to the x-ray diaphragm unit and shielding the x-rays scattered by the object to be examined, wherein the control unit controls a size of an x-ray shielded portion shielded by the second x-ray diaphragm unit by the use of the x-ray diaphragm setting unit.

Thus, since the second x-ray diaphragm mechanically eliminates the x-rays scattered by the object to be examined, it is possible to improve the accuracy of the line noise correction by covering only the scattered x-ray generation portion with the second x-ray diaphragm as well as by increasing the correction data by the use of the data of the covered portion as the data to be used for the line noise correction.

According to another preferred embodiment of this invention, the line noise component obtained by the calculation unit is a predetermined statistical value of data of the x-ray detection element of the x-ray flat panel detector, the data corresponding to the x-ray shielded portion variably set by the x-ray diaphragm setting unit.

Thus, it is possible to suitably perform the line noise correction on data when the data are the cause of the line noise and the predetermined statistical value is useful for the data correction.

According to another preferred embodiment of this invention, the predetermined statistical value is an average value.

Thus, it is possible to suitably perform the line noise correction on data when the data are the cause of the line noise and the average value is useful for the data correction.

According to another preferred embodiment of this invention, the predetermined statistical value is a median.

Thus, it is possible to suitably perform the line noise correction on data when the data are the cause of the line noise and the median is useful for the data correction.

According to another preferred embodiment of this invention, the predetermined statistical value is a value obtained by combining plural statistical values including the average value and the median.

Thus, it is possible to suitably perform the line noise correction on data when the data are the cause of the line noise and the value obtained by combining plural statistical values including the average value and the median is useful for the data correction.

BEST MODE FOR CARRYING OUT THE INVENTION

Hereinafter, preferred embodiments of x-ray diagnostic imaging systems according to this invention will be described in detail using the drawings.

Figure 1:
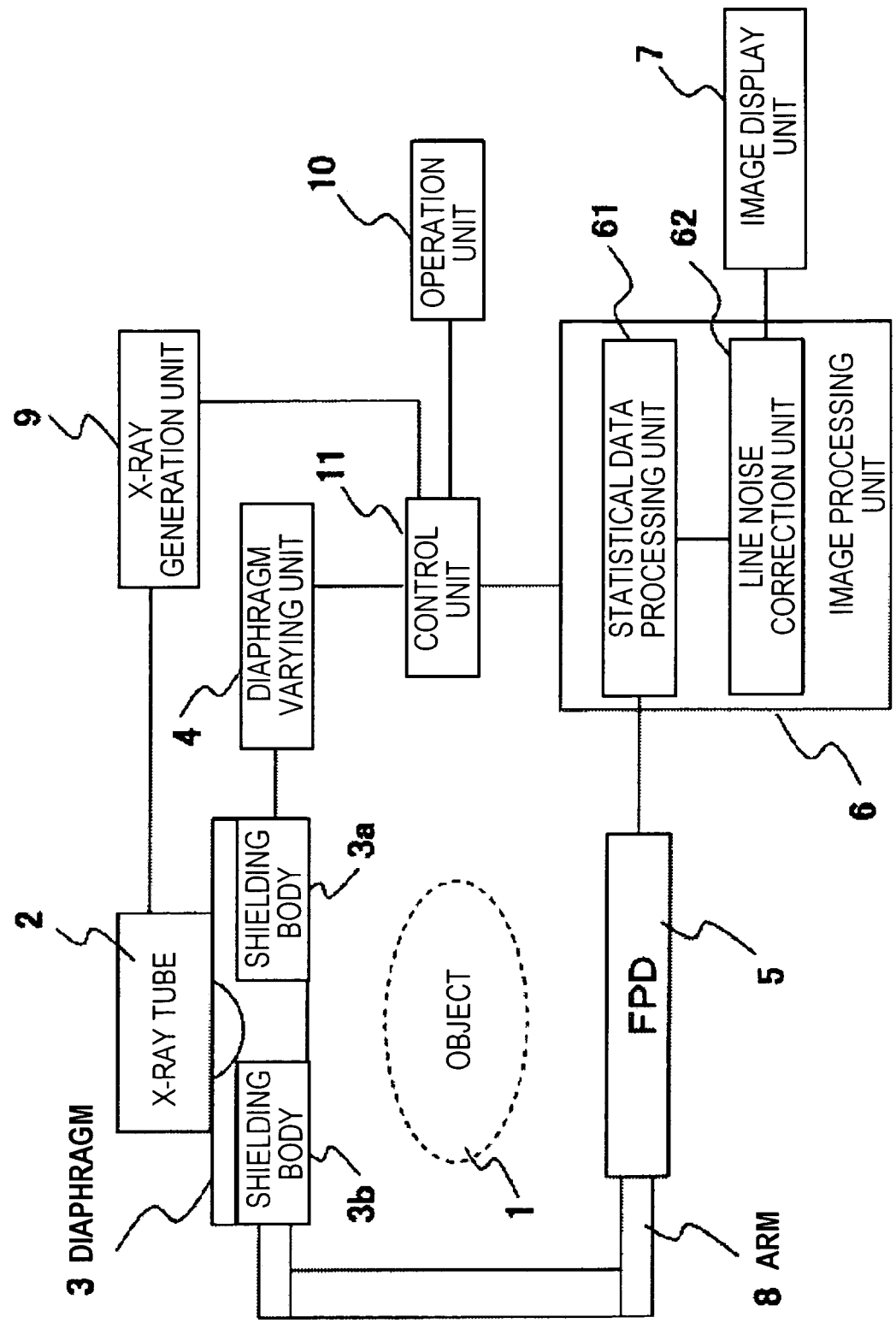
FIG. 1 is a diagram showing one constitution example of an x-ray diagnostic imaging system according to a first embodiment of this invention.

As shown in FIG. 1, an x-ray diagnostic imaging system of a first embodiment has an x-ray tube 2, a diaphragm 3 disposed at an x-ray irradiation side of the x-ray tube 2, a diaphragm varying unit 4 for varying an aperture of the diaphragm 3, an x-ray flat panel detector (hereinafter referred to as FPD which is an abbreviation of Flat Panel Detector) 5 which is opposed to the x-ray tube 2 via an object to be examined 1, an image processing unit 6 electrically connected to the FPD 5, an image display unit 7 electrically connected to the image processing unit 6, an arm 8 supporting the x-ray tube 2 and the FPD 5, an x-ray generation unit 9 electrically connected to the x-ray tube 2, an operation unit 10 which is a parameter input terminal for an operator, and a control unit 11 electrically connected to the diaphragm varying unit 4, the image processing unit 6, and the operation unit 10.

The x-ray tube 2 irradiates the object to be examined 1 with x-rays. The diaphragm 3 shields the irradiated x-rays in such a fashion that only a portion of an x-ray image to be obtained is irradiated with the x-rays. The diaphragm varying unit 4 variably sets an aperture of an opening of the diaphragm 3. The FPD 5 detects x-rays passed through the object to be examined 1 as the x-ray image. The image processing unit 6 performs a signal processing on output signals of the FPD 5. The signal processing includes a gain correction processing on the output signals of the FPD 5, an offset correction processing, a pixel defect correction processing, a tone processing or a recursive filter processing on the x-ray image after the aforementioned correction processings, and the like. The image processing unit 6 has a statistical data processing unit 61 electrically connected to the FPD 5 and a line noise correction unit 62 electrically connected to the statistical data processing unit 61. The statistical data processing unit 61 reads out output signals from the FPD 5 corresponding to the portion shielded by the diaphragm 3 to temporarily store the read out output signals of the shielded portion as data and obtains a line noise component by performing a statistical processing on the temporarily stored data to output the line noise component to the line noise correction unit 62. Examples of a statistical value to be used in the statistical processing include an average value and a median, and any statistical value such as a standard deviation and a variance may be used insofar as it is suitable for the line noise correction. Also, a plurality of the above statistical values may be used in combination. The line noise correction unit 62 subtracts the correction data of the line noise component undergone the statistical processing performed by the statistical data processing unit 61 from the output of the FPD 5 including the line noise to correct the line noise of the x-ray image. The image display unit 7 displays the x-ray image which has been subjected to the image processing by the image processing unit 6. The FPD 5 and the x-ray tube 2 are separately attached to ends of the arm 8 so that they are opposed to each other and supported by the arm 8. The x-ray generation unit 9 is a generator generating a high voltage to be supplied to the x-ray tube 2. The operation unit 10 is an input unit used by the operator for operating the x-ray diagnostic imaging system and provided with an x-ray irradiation switch and an x-ray condition (X-ray tube voltage, X-ray tube current, x-ray irradiation time) setting unit disposed on an operation panel. The control unit 11 performs multiple unit control of the operations of the above-described component parts, calculation of various data, and the like. For instance, in x-ray generation control, the operator inputs the x-ray condition to the operation unit 10, and the control unit 11 sends the input x-ray condition to the x-ray generation unit 9, so that the x-ray generation unit 9 supplies power corresponding to the sent x-ray condition to the x-ray tube 2 and that the x-ray tube 2 emits x-rays of the x-ray condition. Also, in diaphragm control, the operator inputs a size (aperture) of the opening of the diaphragm 3 to the operation unit 10, and the control unit 11 sends the input aperture to the diaphragm varying unit 4, so that the diaphragm varying unit 4 moves the diaphragm 3 to achieve the sent aperture and that the diaphragm 3 forms the aperture set by the operator. Also, in image processing control, the operator inputs condition parameters of image processing to the operation unit 10, and the control unit 11 sends the input condition parameters of image processing to the image processing unit 6 so that the image processing unit 6 performs image processing in accordance with the sent condition parameters. With the arm 8, it is possible to set an arbitrary x-ray irradiation angle with respect to an object to be examined 1 in a state where the opposed position relationship between the x-ray tube 2 and the FPD 5 is maintained.

Figure 2:
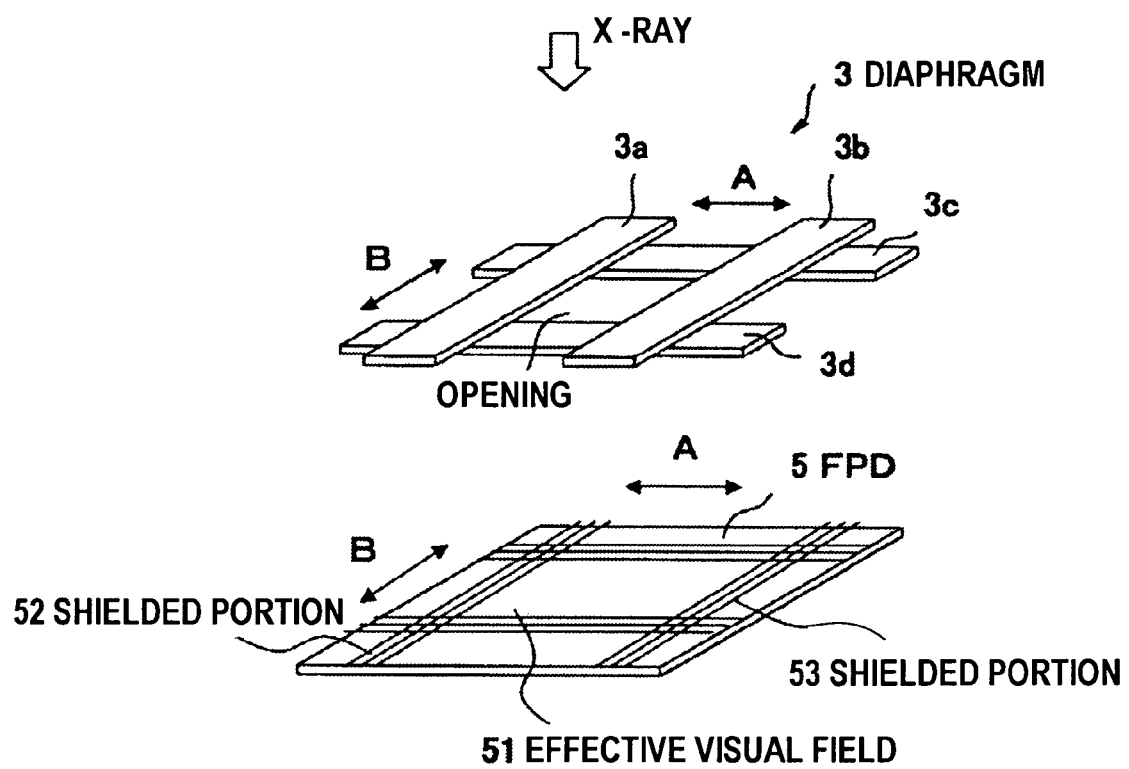
FIG. 2 is a diagram for illustrating a position relationship between an x-ray diaphragm and an FPD.

FIG. 2 is a diagram showing a position relationship with the diaphragm 3 and FPD 5. The diaphragm 3 has four x-ray shielding plates 3a, 3b, 3c, and 3d, for example, and the shielding plates form an opening 52 having a rectangular shape. The shielding plates 3a and 3b move in a direction A, and the shielding plates 3c and 3d move in a direction B which is perpendicular to the direction A. A shadow of the diaphragm 3 is projected on the FPD 5 as shown in FIG. 2. The shadow of the shielding plates 3a and 3b move in the direction A and the shadow of the shielding plates 3c and 3d move in the direction B. Because the data read out from the portion of the projected shadow are used for the line noise correction, the shadow portion is referred to as shielded portion in this specification. For the brevity of description, only the shielded portions 52 and 53 in the direction A will be described. The portion used for obtaining the x-rays passed through the object to be examined 1 is a visual field 51 corresponding to the opening of the diaphragm 3. Since mechanism of the diaphragm 3 has been known in the art of this invention, a specific example of a driving mechanism of the diaphragm 3 is omitted in this specification.

Figure 3:
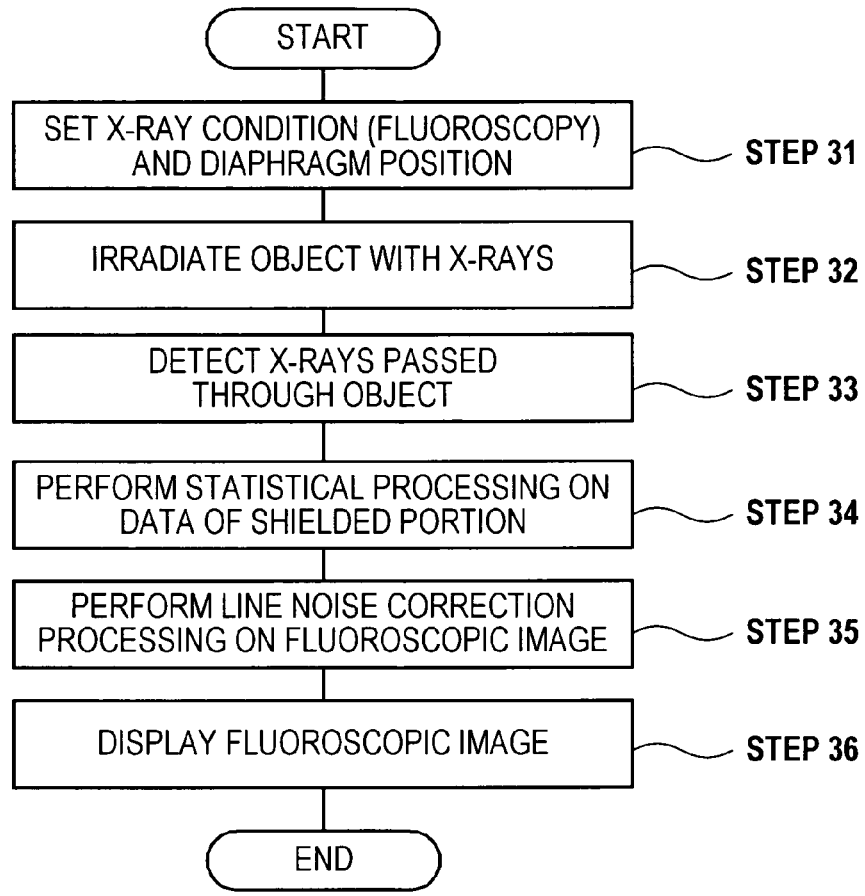
FIG. 3 is a flowchart showing one example of processing of the x-ray diagnostic imaging system of FIG. 1.

One operation example of the first embodiment will be described using FIG. 3.

An operator uses the operation unit 10 for setting an x-ray condition for obtaining a fluoroscopic image to the x-ray tube 2 as well as for setting an aperture of the diaphragm 3 to the x-ray diaphragm varying unit 4 (Step 31).

The x-ray tube 2 irradiates the object to be examined 1 with x-rays corresponding to the set x-ray condition (Step 32).

FPD 5 detects image data for the x-rays irradiated on and passed through the object to be examined 1 and detects data of the shielded portions 52 and 53 (Step 33).

The statistical data processing unit 61 of the image processing unit 6 performs statistical processing calculation of the data of the shielded portions to obtain a statistical value of a line noise component (Step 34).

The line noise correction unit 62 of the image processing unit 6 subtracts the obtained statistical value of the line noise component from the detected x-ray image data to correct a line noise of the x-ray image data (Step 35).

The image display unit 7 displays an image of the corrected x-ray image data (Step 36).

For instance, in the case of checking a catheter or a guide wire at a treatment area in an object to be examined, an operator operates the diaphragm 3 to set the visual field 51 in accordance with the catheter or the like. In this case, since it is possible to use wider shielded portions, the line noise component is obtained from the increased detection data, and, since the increased detection data are subjected to the statistical processing, accuracy of calculation of the line noise component is increased, resulting in displaying a fluoroscopic image on the display 27. Thus, it is possible to accurately perform the line noise correction of x-ray image by the use of the data of the shielded portions of the x-ray diaphragm which is variably set by the x-ray diaphragm setting unit.

In this embodiment, since the x-ray shielding material is fixed to the FPD 5 as in Patent Literature 1, it is possible to effectively use the overall FPD 5 in the case of capturing images which do not require the line noise correction. Further, in the case of a fluoroscopic image, it is possible to correct the line noise of the x-ray image by effectively using the x-ray non-irradiation portion of the x-ray flat panel detector, the x-ray non-irradiation portion being varied thanks to the variably set x-ray diaphragm.

Alternatively, the statistical value of the line noise component may be an average value of data read out from the x-ray detection elements in this embodiment.

Thus, it is possible to suitably perform the line noise correction on data when the data are the cause of the line noise and the average value is useful for the data correction.

Alternatively, the statistical value of the line noise component may be a median of the data read out from the x-ray detection elements in this embodiment.

Thus, it is possible to suitably perform the line noise correction on data when the data are the cause of the line noise and the median is useful for the data correction.

Alternatively, the statistical value of the line noise component may be a value obtained by combining statistical values such as the average value and the median of the data read out from the x-ray detection elements in this embodiment.

Thus, it is possible to suitably perform the line noise correction on data when the data are the cause of the line noise and the statistical value obtained by combining statistical values is useful for the data correction.

Figure 4:
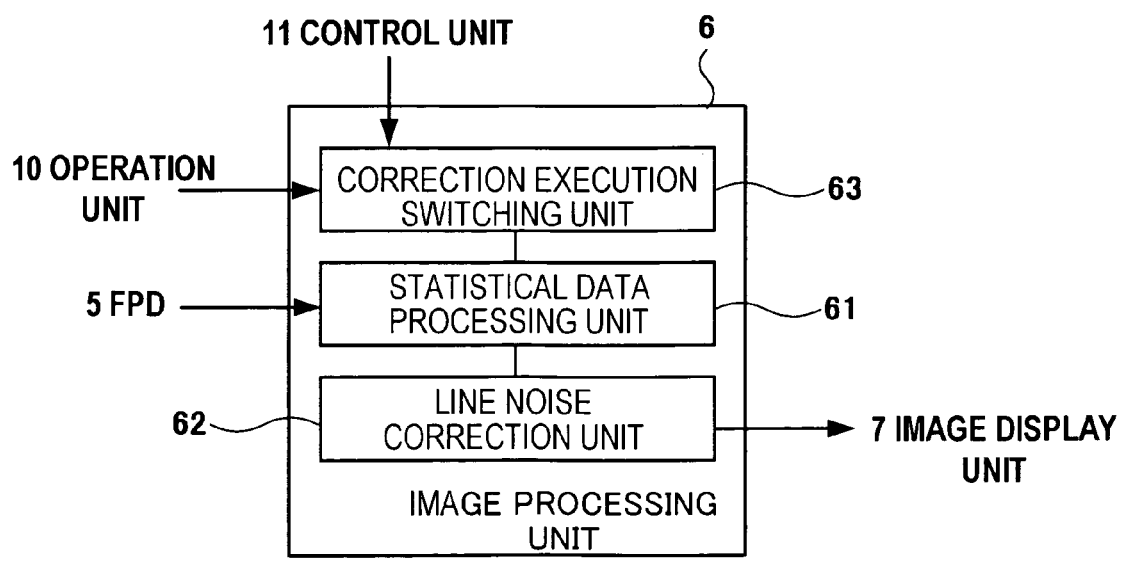
FIG. 4 is a diagram showing one constitution example of an image processing unit of an x-ray diagnostic imaging system according to a second embodiment of this invention.
Figure 5:
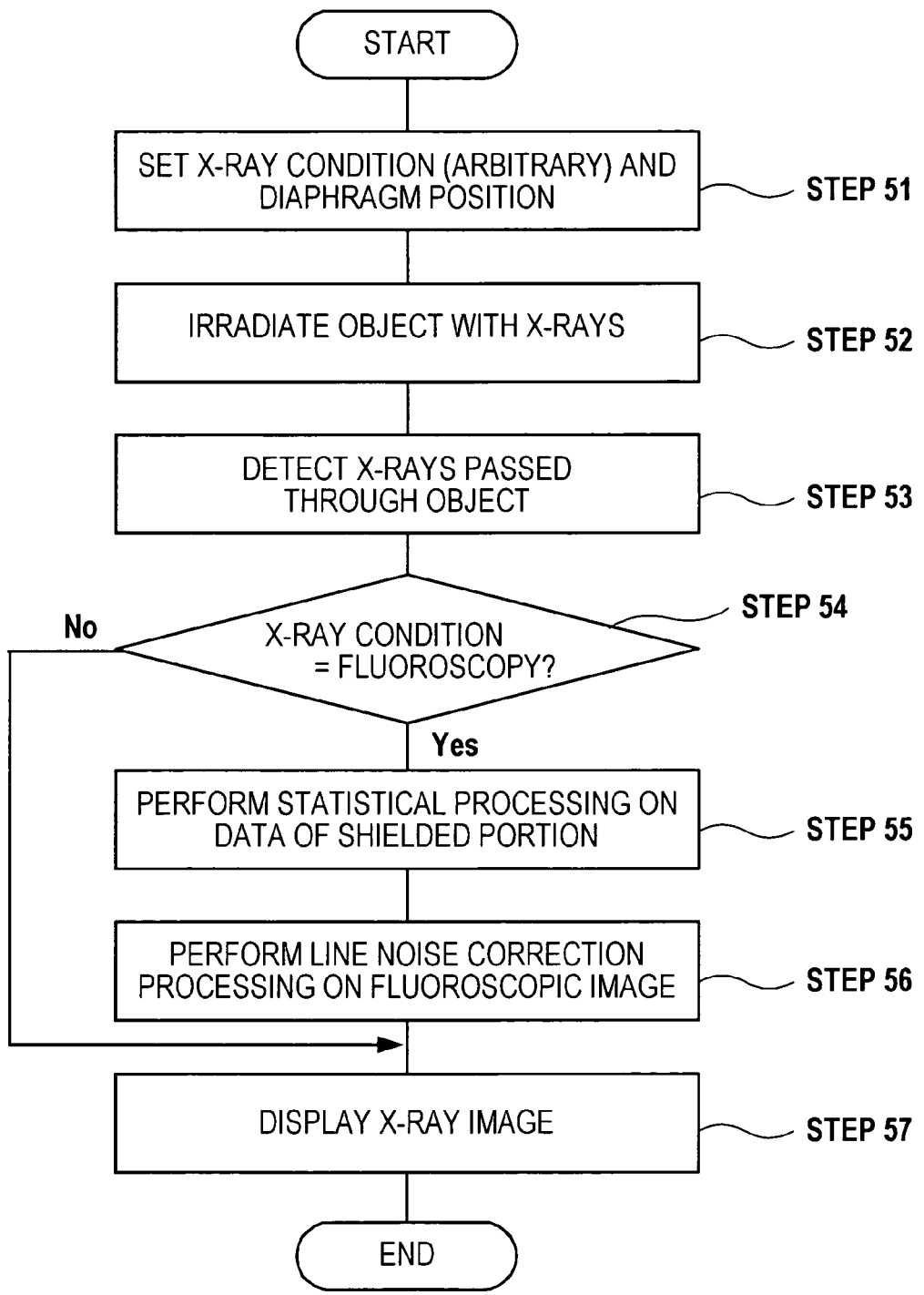
FIG. 5 I a flowchart showing one example of processing of the x-ray diagnostic imaging system of FIG. 4.

Hereinafter, a second embodiment of this invention will be described using FIGS. 4 and 5.

The second embodiment is suitable for the cases wherein an x-ray image pickup is performed by successively performing a mode (fluoroscopic mode) for obtaining a fluoroscopic image which requires the line noise correction and a mode (radiographic mode) for obtaining a radiographic image which almost never requires the line noise correction.

Difference of the x-ray diagnostic imaging system of this embodiment from the first embodiment is that a correction execution switching unit 63 electrically connected to the operation unit 10 is added to the image processing unit 6. The correction execution switching unit 63 has a function of a multiplexer which switches over the fluoroscopic mode where the line noise correction should be executed and the radiographic mode where the line noise correction should not be executed based on judgment of the modes.

One example of the second embodiment will be described using FIG. 5.

An operator uses the operation unit 10 for setting an x-ray condition for obtaining a fluoroscopic image to the x-ray tube 2 as well as for setting an aperture of the diaphragm 3 to the x-ray diaphragm varying unit 4 (Step 51).

The x-ray tube 2 irradiates the object to be examined 1 with x-rays corresponding to the set x-ray condition (Step 52).

The FPD 5 detects image data for the x-rays irradiated on and passed through the object to be examined 1 and detects data of the shielded portions 52 and 53. Though the data detections of the shielded portions are performed at this time point in this case, the data detection may be performed before Step 55 without being performed in this step (Step 53).

The correction execution switching unit 63 of the image processing unit 6 judges whether or not the fluoroscopic (radiographic) mode is set in the x-ray condition. As a result of the judgment, the process proceeds to Step 55 when the fluoroscopic mode is set or to Step 57 when the radiographic mode is set (step 54).

The statistical data processing unit 61 of the image processing unit 6 performs statistical processing calculation of the data of the shielded portions to obtain a statistical value of a line noise component (Step 55).

The line noise correction unit 62 of the image processing unit 6 subtracts the obtained statistical value of the line noise component from the detected x-ray image data to correct a line noise of the x-ray image data (Step 56).

The image display unit 7 displays an image of the corrected x-ray image data (Step 57).

When the correction execution switching unit 63 is turned off, it is possible to return to the manual mode of the first embodiment operated by the operator.

According to the second embodiment, by prescribing the setting for executing the line noise correction in the x-ray condition, the correction mode is switched on only for the fluoroscopic mode in the case where the fluoroscopic mode and the radiographic mode are successively performed; therefore, operability is improved because it is needless to set the necessity/non necessity of correction for every switching between the modes.

Figure 6:
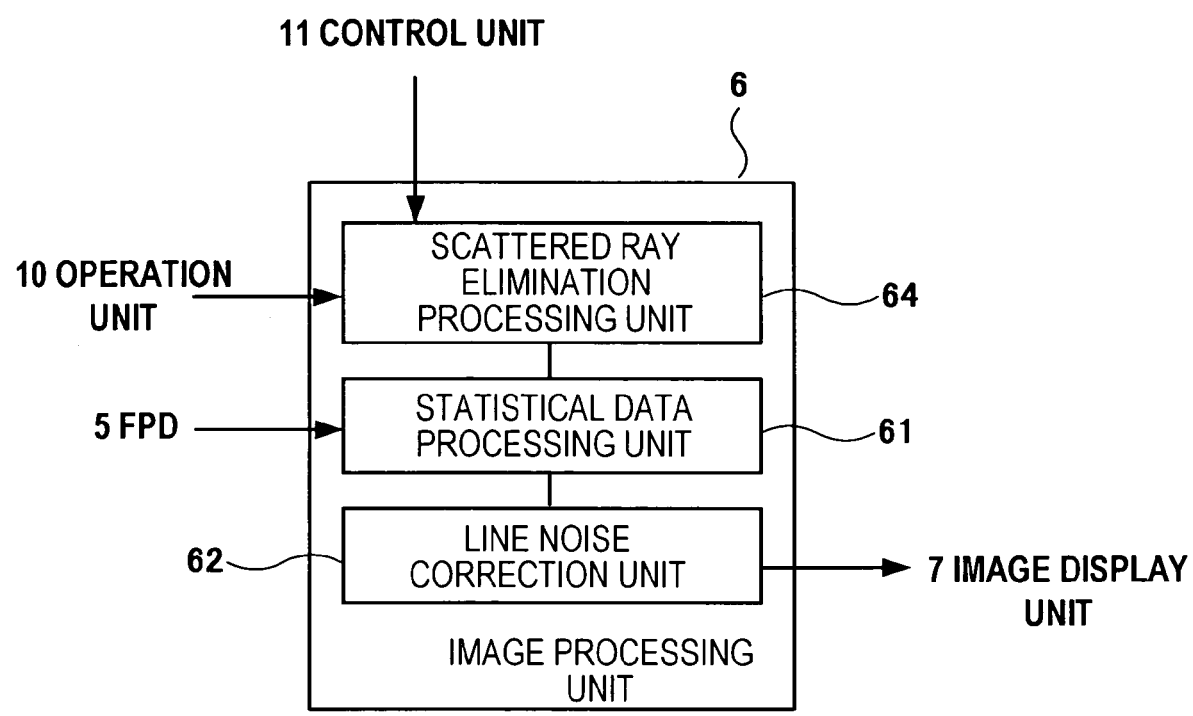
FIG. 6 is a diagram showing one constitution example of an image processing unit of an x-ray diagnostic imaging system according to a third embodiment of this invention.
Figure 7:
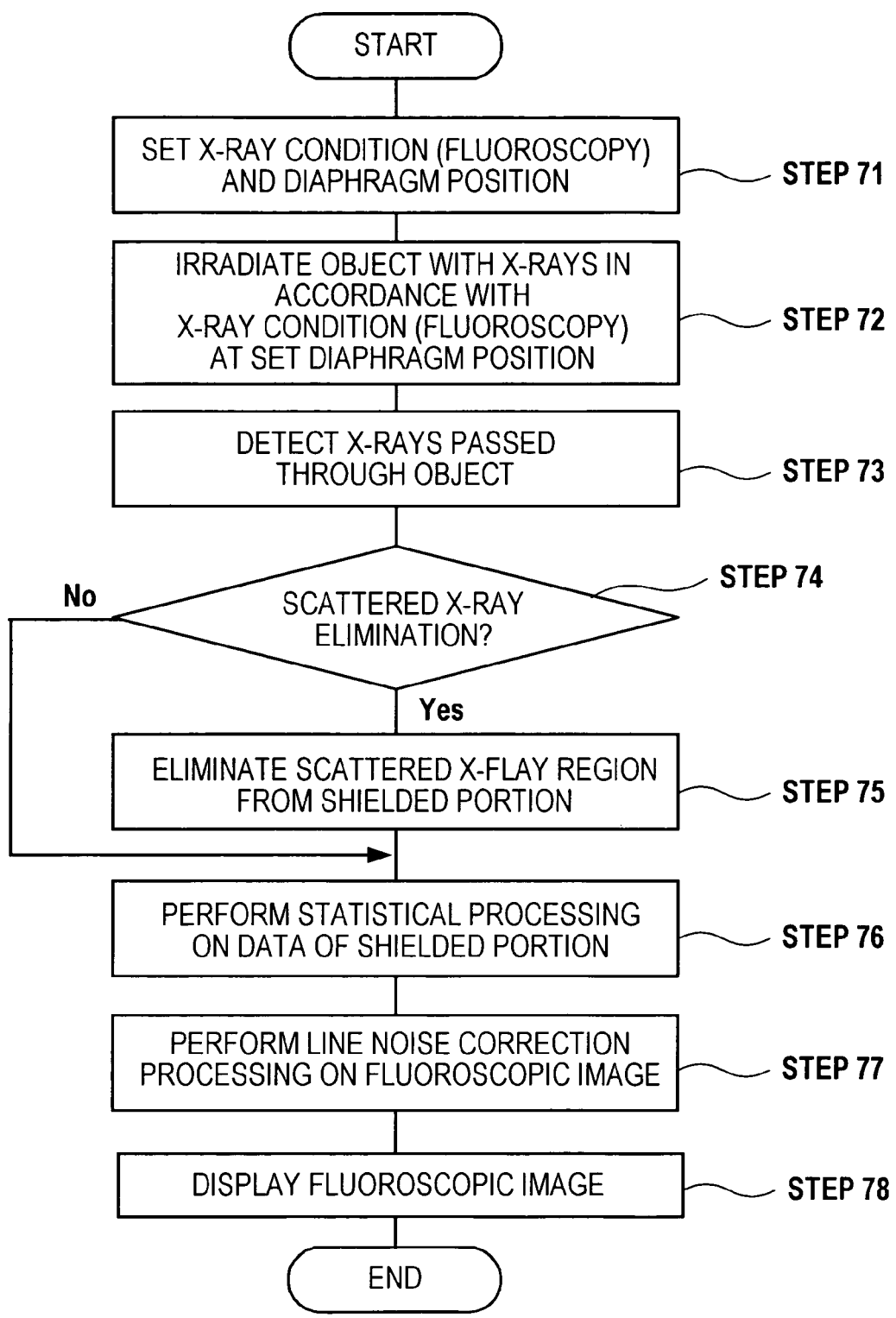
FIG. 7 is a flowchart showing one example of processing of the x-ray diagnostic imaging system of FIG. 6.

A third embodiment of this invention will be described by using FIGS. 6 and 7.

The third embodiment considers elimination of influences of x-rays scattered by the object to be examined 1.

Difference of the x-ray diagnostic imaging system of this embodiment from the first embodiment is that a scattered ray elimination processing unit 64 electrically connected to the operation unit 10 is added to the image processing unit 6. The x-rays scattered by the object to be examined 1 and input to the shielded portions of the FPD 5 shielded by the diaphragm 3 cause detection of incident x-rays in the shielded portions though such x-rays should not be detected under normal circumstances. The scattered ray elimination processing unit 64 performs such a processing that, when a detection value of the shielded portions of the FPD 5 in which the x-rays are not supposed to enter exceeds a predetermined threshold value, the shielded portions are not used for the calculation for obtaining the line noise component.

One operation example of the third embodiment will be described using FIG. 7.

An operator uses the operation unit 10 for setting an x-ray condition for obtaining a fluoroscopic image to the x-ray tube 2 as well as for setting an aperture of the diaphragm 3 to the x-ray diaphragm varying unit 4 (Step 71).

The x-ray tube 2 irradiates the object to be examined 1 with x-rays corresponding to the set x-ray condition (Step 72).

The FPD 5 detects image data for the x-rays irradiated on and passed through the object to be examined 1 and detects data of the shielded portions 52 and 53. Though the data detections of the shielded portions are performed at this time point in this case, the data detection may be performed before Step 75 without being performed in this step (Step 73).

The scattered ray elimination processing unit 64 of the image processing unit 6 judges whether or not the x-rays scattered by the object to be examined 1 are detected in the shielded portions of the FPD 5 shielded by the diaphragm 3 and whether or not the detection value exceeds the predetermined threshold value. As a result of the judgment, the process proceeds to Step 75 when the detected value exceeds the threshold value or to Step 76 when the detected value does not exceed the threshold or the mode is the radiographic mode (Step 74).

The scattered ray elimination processing unit 64 of the image processing unit 6 sends the information of the portions in which the detection value has exceeded the threshold value (portions to which much x-rays are made incident)

to the statistical data processing unit 61 to eliminate the scattered x-ray generation area from the shielded portions (Step 75).

The statistical data processing unit 61 of the image processing unit 6 performs statistical processing calculation of the data of the shielded portions to obtain a statistical value of a line noise component (Step 76).

The line noise correction unit 62 of the image processing unit 6 subtracts the obtained statistical value of the line noise component from the detected x-ray image data to correct a line noise of the x-ray image data (Step 77).

The image display unit 7 displays an image of the corrected x-ray image data (Step 78).

According to the third embodiment, it is possible to obtain a high quality x-ray image since the data to be used for the line noise correction are not influenced by the scattered x-rays.

Figure 8:
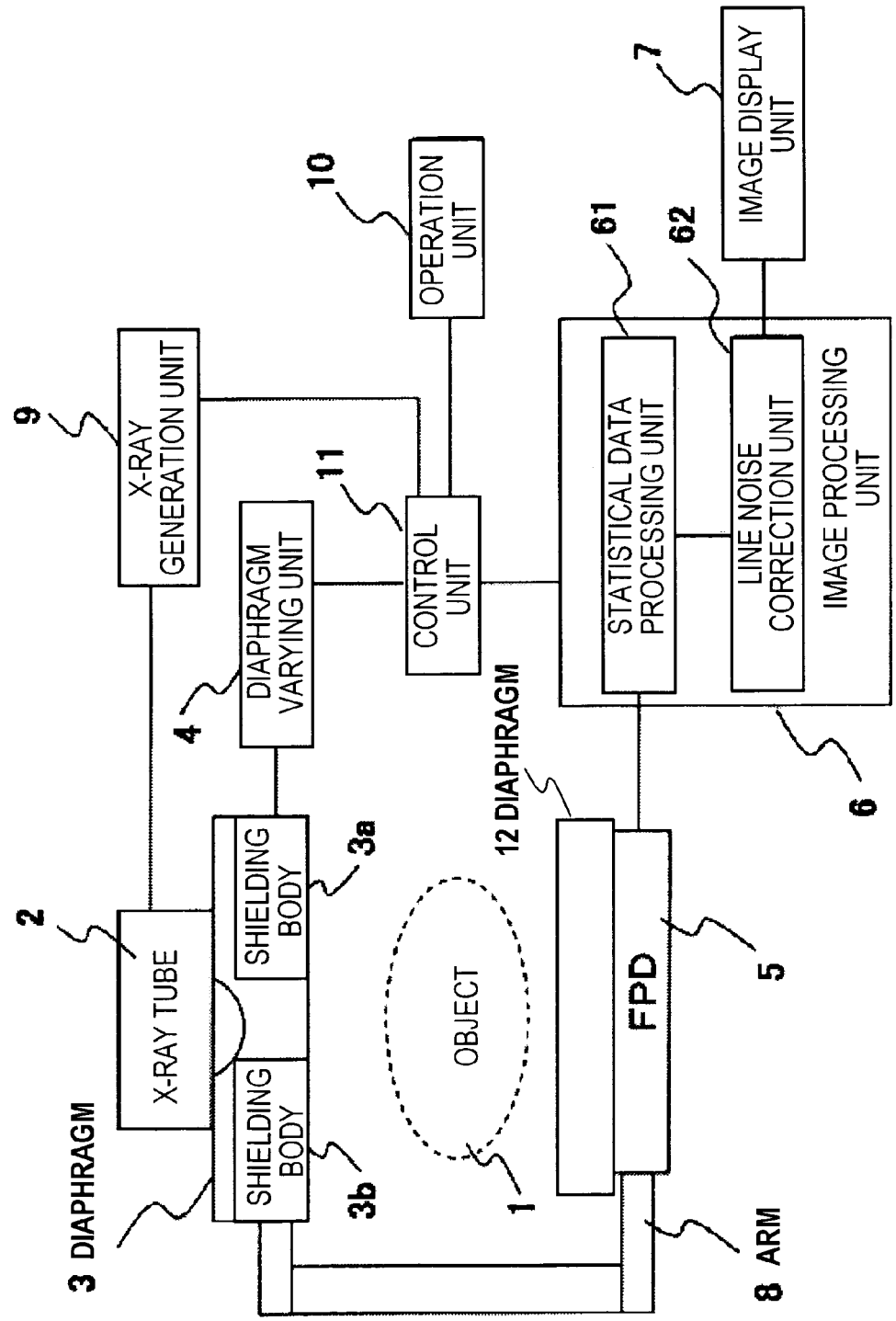
FIG. 8 is a diagram showing one constitution example of an image processing unit of an x-ray diagnostic imaging system according to a fourth embodiment of this invention.
Figure 9:
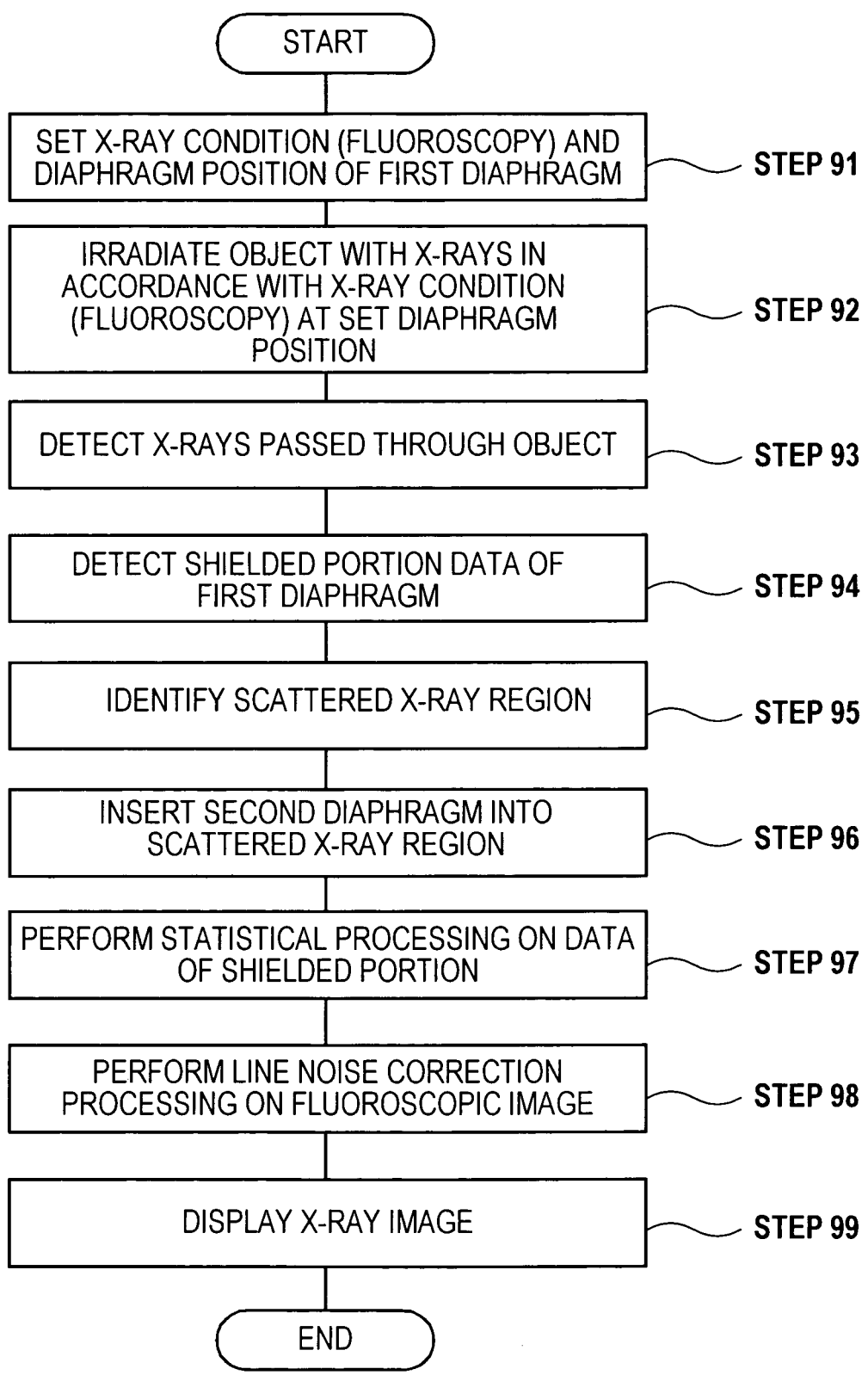
FIG. 9 is a flowchart showing one example of processing of the x-ray diagnostic imaging system of FIG. 8.

Hereinafter, a fourth embodiment of this invention will be described by using FIGS. 8 and 9.

The fourth embodiment considers a further improvement in accuracy of the line noise correction by eliminating the x-rays scattered by the object to be examined 1 by the use of a second diaphragm 12 and by increasing a portion to be used for the line noise correction by the use of a shadow of the second diaphragm 12.

Difference of the x-ray diagnostic imaging system of this embodiment from the first embodiment is that the second diaphragm 12 is added between the object to be examined 1 and the FPD 5. The second diaphragm 12 shields the x-rays scattered by the object to be examined 1 as described in the third embodiment.

One operation example of the fourth embodiment will be described by using FIG. 9.

An operator uses the operation unit 10 for setting an x-ray condition for obtaining a fluoroscopic image to the x-ray tube 2 as well as for setting an aperture of the diaphragm (first diaphragm) 3 to the x-ray diaphragm varying unit 4 (Step 91).

The x-ray tube 2 irradiates the object to be examined 1 with x-rays corresponding to the set x-ray condition (Step 92).

The FPD 5 detects image data for the x-rays irradiated on and passed through the object to be examined 1 (Step 93).

The FPD 5 detects data of the shielded portions 52 and 53 (Step 94).

The control unit 11 performs the threshold value processing described in the third embodiment on the detected data of the shielded portions 52 and 53 so as to identify a portion (scattered X-ray region) where scattered x-rays are generated in the data of the shielded portions 52 and 53 (Step 95).

The diaphragm varying unit 4 inserts the second diaphragm 12 into the scattered X-ray region to add the scattered ray portion to the shielded portions (Step 96).

The statistical data processing unit 61 of the image processing unit 6 performs statistical processing calculation of the data of the shielded portions (including the added portions) to obtain a statistical value of a line noise component (Step 97).

The line noise correction unit 62 of the image processing unit 6 subtracts the obtained statistical value of the line noise component from the detected x-ray image data to correct a line noise of the x-ray image data (Step 98).

The image display unit 7 displays an image of the corrected x-ray image data (Step 99).

According to the fourth embodiment, since the second x-ray diaphragm mechanically eliminates the x-rays scattered by the object to be examined, it is possible to improve the accuracy of the line noise correction by covering the scattered x-ray generation portion with the second x-ray diaphragm as well as by increasing the correction data by the use of the data of the covered portion as the data to be used for the line noise correction.

Though plural embodiments of this invention have been described in the foregoing, this invention is not limited to the above-described embodiments, and all technical contents realizing the technical idea defined in claims are encompassed by this invention.

INDUSTRIAL APPLICABILITY

This invention provides an x-ray diagnostic imaging system capable of effectively using an x-ray irradiation portion of an x-ray flat panel detector in accordance with an x-ray diaphragm varied based on an x-ray image acquisition mode such as a fluoroscopic mode and a radiographic mode.

The invention claimed is:

1. An x-ray diagnostic imaging system comprising:
   an x-ray irradiation unit for irradiating an object to be examined with x-rays;
   an x-ray diaphragm unit disposed in a direction of x-ray irradiation of the x-ray irradiation unit and shielding the irradiated x-rays except for the x-rays irradiated on a portion used for obtaining an x-ray image of the object to be examined;
   an x-ray diaphragm setting unit for variably setting the x-ray shielded portion to be shielded by the x-ray diaphragm unit;
   an x-ray flat panel detector opposed to the x-ray irradiation unit via the object to be examined and imaging x-rays passed through the object to be examined as an x-ray image;
   an image processing unit for subjecting the x-ray image obtained by the x-ray flat panel detector to an image processing; and
   a display unit displaying the x-ray image subjected to the image processing by the image processing unit, wherein
   the image processing unit comprises:
   a calculation unit reading out data of an x-ray detection element of the x-ray flat panel detector corresponding to the x-ray shielded portion shielded by the x-ray diaphragm unit which is variably set by the x-ray diaphragm setting unit and calculating a line noise component from the read out data of the x-ray detection element; and
   a line noise correction unit correcting a line noise of the x-ray image based on the line noise component calculated by the calculation unit.

2. The x-ray diagnostic imaging system according to claim 1, wherein the calculation unit includes interaction of a data portion read out as the line noise component from the x-ray flat panel detector with the x-ray diaphragm unit variably set by the x-ray diaphragm setting unit.

3. The x-ray diagnostic imaging system according to claim 1, wherein the image processing unit further comprises a correction execution switching unit switching to execution/non-execution of the line noise correction based on an x-ray condition set to the x-ray irradiation unit.

4. The x-ray diagnostic imaging system according to claim 1, wherein the image processing unit further comprises a scattered x-ray elimination processing unit identifying an area in which x-rays scattered by the object to be examined are generated on the x-ray flat panel detector corresponding to the x-ray shielded portion variably set by the x-ray diaphragm setting unit and eliminating the identified scattered x-ray generation area from the line noise component calculation performed by the calculation unit.

5. The x-ray diagnostic imaging system according to claim 1, further comprising a second x-ray diaphragm unit disposed between the object to be examined and the x-ray flat panel detector in addition to the x-ray diaphragm unit and shielding the x-rays scattered by the object to be examined, wherein the x-ray diaphragm setting unit variably sets a size of an x-ray shielded portion shielded by the second x-ray diaphragm unit.

6. The x-ray diagnostic imaging system according to claim 1, further comprising:
  an operation unit to be used by an operator for setting an x-ray condition to the x-ray irradiation unit, an aperture condition of the x-ray diaphragm unit to the x-ray diaphragm setting unit, and an operation condition to the image processing unit; and
  a control unit driving the x-ray irradiation unit, the x-ray diaphragm setting unit, and the image processing unit based on the conditions set by the operation unit.

7. The x-ray diagnostic imaging system according to claim 6, wherein the control unit causes the x-ray irradiation unit to irradiate the object to be examined with x-rays corresponding to the x-ray condition set by the operation unit; the x-ray flat panel detector detects x-ray image data of x-rays projected by the x-ray irradiation unit and passed through the object to be examined and data of the shielded portion shielded by the x-ray diaphragm unit; and the calculation unit calculates a line noise component from the shielded portion data detected by the x-ray flat panel detector.

8. The x-ray diagnostic imaging system according to claim 6, wherein the line noise component obtained by the calculation unit is a predetermined statistical value of data of the x-ray detection element of the x-ray flat panel detector, the data corresponding to the x-ray shielded portion variably set by the x-ray diaphragm setting unit.

9. The x-ray diagnostic imaging system according to claim 6, wherein the control unit controls the correction execution switching unit switching to execution/non-execution of the line noise correction based on the x-ray condition set by the operation unit.

10. The x-ray diagnostic imaging system according to claim 6, wherein the control unit controls a scattered x-ray elimination processing unit identifying an area in which x-rays scattered by the object to be examined are generated on the x-ray detection element of the x-ray flat panel detector corresponding to the x-ray shielded portion variably set by the x-ray diaphragm setting unit and eliminating the identified scattered x-ray generation area from the line noise component calculation performed by the calculation unit.

11. The x-ray diagnostic imaging system according to claim 6, further comprising a second x-ray diaphragm unit disposed between the object to be examined and the x-ray flat panel detector in addition to the x-ray diaphragm unit and shielding the x-rays scattered by the object to be examined, wherein the control unit controls a size of an x-ray shielded portion shielded by the second x-ray diaphragm unit by the use of the x-ray diaphragm setting unit.

12. The x-ray diagnostic imaging system according to claim 1, wherein the line noise component obtained by the calculation unit is a predetermined statistical value of data of the x-ray detection element of the x-ray flat panel detector, the data corresponding to the x-ray shielded portion variably set by the x-ray diaphragm setting unit.

13. The x-ray diagnostic imaging system according to claim 12, wherein the predetermined statistical value is an average value.

14. The x-ray diagnostic imaging system according to claim 12, wherein the predetermined statistical value is a median.

15. The x-ray diagnostic imaging system according to claim 12, wherein the predetermined statistical value is a value obtained by combining plural statistical values including the average value and the median.

16. The x-ray diagnostic imaging system according to claim 1, wherein the visual field of the diaphragm unit is set in accordance with a catheter or guide wire.

17. The x-ray diagnostic imaging system according to claim 1, further comprising means for performing line noise correction for a fluoroscopic image using data from the shielded portion.

* * * * *